United States Patent
Burkhardt et al.

(10) Patent No.: US 6,456,944 B1
(45) Date of Patent: Sep. 24, 2002

(54) AUTOMATIC ANALYZER FOR MONITORING PIPETTING OPERATIONS

(75) Inventors: Claudius Burkhardt, Lucerne (CH); Fritz Gödl, Rotkreuz (CH)

(73) Assignee: Roche Diagnostics Corporation, Indianapolis, IN (US)

( * ) Notice: Subject to any disclaimer, the term of this patent is extended or adjusted under 35 U.S.C. 154(b) by 0 days.

(21) Appl. No.: 09/399,554

(22) Filed: Sep. 20, 1999

(30) Foreign Application Priority Data

Sep. 30, 1998 (EP) .............................. 98810985

(51) Int. Cl.$^7$ .................... G01N 35/00; G01N 35/10
(52) U.S. Cl. ............... 702/32; 73/863.01; 73/864.21; 73/864.22; 422/67; 422/68.1
(58) Field of Search .................. 702/32, 25, 30, 702/31; 73/863.01, 863.02, 863.03, 864.21, 864.22, 864.23, 864.24, 864.25; 422/67, 68.1

(56) References Cited

U.S. PATENT DOCUMENTS

| | | | |
|---|---|---|---|
| 4,326,851 A | * 4/1982 | Bello et al. | .......... 73/864.24 X |
| 4,794,085 A | * 12/1988 | Jessop et al. | ......... 73/863.01 X |
| 4,893,515 A | 1/1990 | Uchida | .................... 73/864.34 |
| 4,963,498 A | * 10/1990 | Hillman et al. | ......... 422/68.1 X |
| 5,012,683 A | * 5/1991 | Davis | ..................... 73/864.24 |
| 5,265,482 A | 11/1993 | Davis et al. | ............ 73/863.01 |
| 5,314,825 A | * 5/1994 | Weyrauch et al. | ........ 422/67 X |
| 5,478,747 A | * 12/1995 | Hertz, Jr. | ...................... 436/45 |
| 5,493,922 A | * 2/1996 | Ramey et al. | ........... 73/863.02 |
| 2001/0007769 A1 | * 7/2001 | Wagner | ...................... 436/43 |

FOREIGN PATENT DOCUMENTS

| | | | | |
|---|---|---|---|---|
| EP | 210014 A2 | * | 1/1987 | .............. 73/864.21 |
| EP | 289946 A2 | * | 11/1988 | .......... G01N/35/06 |
| EP | 0 672 906 A1 | | 9/1995 | .......... G01N/35/00 |
| EP | 694784 A1 | * | 1/1996 | .......... G01N/35/60 |
| EP | 0 726 466 A1 | | 8/1996 | .......... G01N/35/26 |
| WO | WO 95 00829 | | 1/1995 | ............ G01N/3/06 |

* cited by examiner

Primary Examiner—Thomas P. Noland
(74) Attorney, Agent, or Firm—Gibbons, Del Deo, Dolan, Griffinger & Vecchione

(57) ABSTRACT

An automatic analyzer for the assay of liquid samples pipetted from a container into a mixing chamber includes a controller for controlling the operation of the analyzer in response to sensors that monitor the functions of the analyzer. Within the analyzer, the responses of the sensors are evaluated and, when such responses do not meet prescribed criteria, error messages are provided. In the disclosed embodiments, the controller is implemented using at least one program-controlled processor. In order to monitor the pipetting operations in an effective manner, the automatic analyzer, in one embodiment, uses a plurality of operation and monitoring control units which operate independently of one another. Each of these units is by a central processing unit.

5 Claims, 4 Drawing Sheets

AUTOMATIC ANALYZER FOR MONITORING PIPETTING OPERATIONS

FIELD OF THE INVENTION

The invention refers to an automatic analyzer for the assay of liquid samples.

BACKGROUND OF THE INVENTION

Automatic analyzers for the analysis of liquid samples of biological substances such as blood or urine are well known. FIG. 1 schematically shows the block diagram of a prior art automatic analyzer 10. Samples are provided in separate containers, e.g. on an array 11. By means of an automatic pipetting device 12, small amounts of the samples are transferred to a mixing chamber 14 in a serial manner. Chamber 14 is an upwardly open reaction cuvette connected to inlet openings 15 and 16 for air and water, respectively, to homogenize the respective liquid sample in order to rinse the chamber. Excess liquid or washing liquid (waste) may be evacuated through a first outlet opening 17. Through a second outlet opening, i.e. a connecting tube 21, the diluted liquid sample is supplied to the measuring channel of a block of electrodes 22 which allows measurement of the concentration of ions, e.g. $Li^+$, $K^+$, $Na^+$, $Cl^-$, by means of ion-selective electrodes. Finally, the liquid sample is discharged through an outlet 23 for destruction.

The described arrangement is associated with a comprehensive electronic control, surveillance, and evaluation system 24 which controls and monitors the pipetting operations for taking samples from the sample containers of array 11 and for transferring each of the samples to a reaction cuvette of a mixing chamber 14. This electronic control system comprises program-controlled microprocessors.

The operation of automatic analyzers of the kind represented in FIG. 1 should be as trouble free as possible. However, for various reasons, this aim can only be attained within certain limits. In particular, frequent problems are caused by small particles such as blood clots which may choke the pipetting needle and other parts of the analyzer, thereby resulting in analysis errors or even rendering the measurements impossible. Therefore, it is desirable to provide devices to monitor the pipetting operations as effectively as possible. This can be achieved by monitoring the pressure values during aspiration and ejection of the liquid samples into and out of the pipetting needles, respectively. Attempts of this kind are known from WO 95/00829, U.S. Pat. No. 4,794,085, EP-A-0 289 946, and EP-A-0 210 014.

Another known monitoring device is related to controlling an accurate immersion depth of the tip of the pipetting needle into the liquid sample. Such control is necessary when the sample liquids contained in the sample containers of array 11 have different level heights. For instance, references U.S. Pat. No. 5,493,922, EP-A- 0 694 784, U.S. Pat. Nos. 5,012,683, and 4,326,851 describe known devices for controlling the immersion depth of the tip of the pipetting needle into a liquid sample. A known control device of this kind uses a high frequency field for that purpose.

Other methods involving use of optical means for controlling the immersion depth of the tip of the pipetting needle are also known.

SUMMARY OF THE INVENTION

In view of the foregoing, the aim of the present invention is to provide an automatic analyzer which allows highly effective monitoring of pipetting operations. This means that the number of failures and measuring errors are far lower than in comparable analyzers of the prior art. This results in a substantial reduction of operating time losses and improved accuracy and reliability of measurement results.

According to the present invention, this aim is achieved by an automatic analyzer comprising:

a pipetting device for removing the liquid sample from a container and for transferring the sample, a mixing chamber having a reaction cuvette for receiving the sample, means for controlling the operation of the analyzer, sensors for monitoring the function of the analyzer, means for evaluating possible monitoring results and for delivering possible error messages, whereby the means include at least one program-controlled processor, a plurality of operation and monitoring control units which are independent from each other, a central processing unit for activating each of the control units by a start command and for carrying out a process which ends with the delivery of a corresponding mode signal (S1 to S7) to the central processing unit, and a combinatory logic circuit which is connected to at least two of the control units, the logic circuit combining messages delivered by the control units as a logical AND and delivers to the central processing unit an output mode signal which corresponds to the combinatory result, and reactions of the analyzer each of which corresponds to each one of the mode signals (S1 to S7) being provided in the central processing unit.

The automatic analyzer of the present invention provides numerous advantages over the prior art. The extended control and monitoring possibilities provided by the automatic analyzer of the invention result in significant improvement of the reliability and accuracy of the operation of the analyzer as previously mentioned.

DETAILED DESCRIPTION OF THE INVENTION

Figure 1:
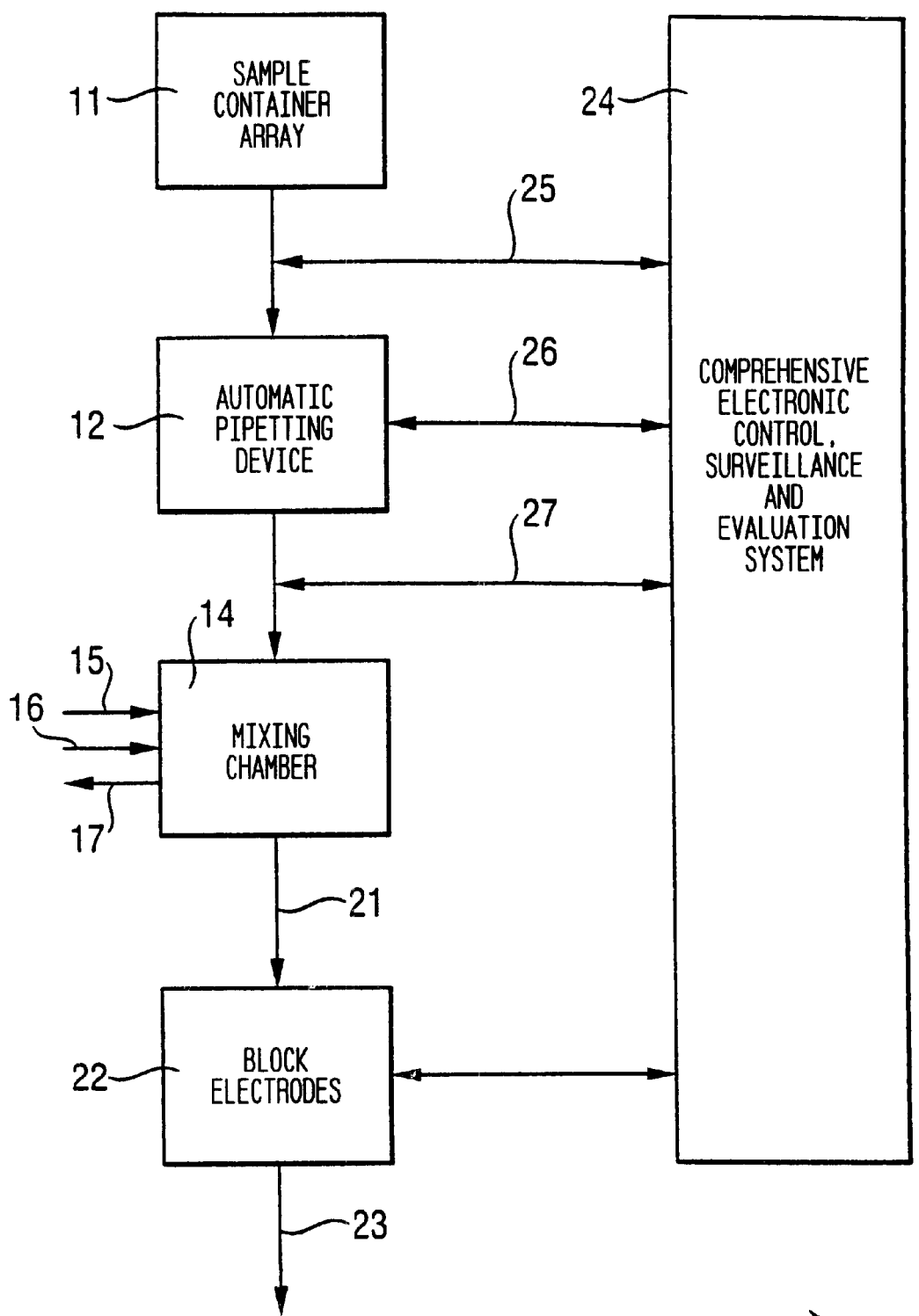
FIG. 1 shows a block diagram of a prior art automatic analyzer.
Figure 2:
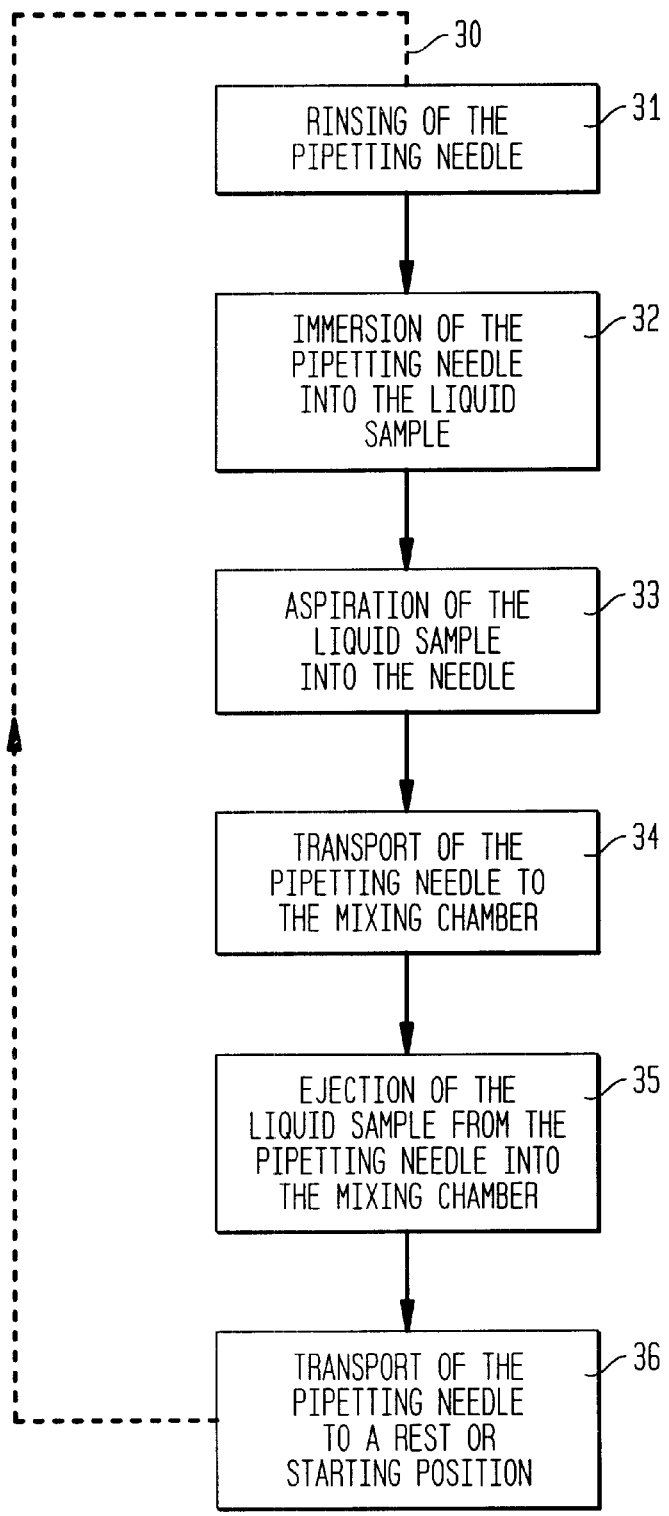
FIG. 2 shows a flow diagram of sequences of operations related to a pipetting process.

FIG. 2 shows a flow diagram of a sequence of processes 31–36 for taking a sample from a container of a sample container array 11 (FIG. 1) and transferring the sample to a reaction cuvette of a mixing chamber 14 (FIG. 1) by means of a pipetting device. This sequence of processes 31–36 is launched by a start command 30 which starts process 31 which causes rinsing of the pipetting needle. Process 31 is followed by:

process 32 which causes immersion of the point of the pipetting needle into the liquid sample, process 33 which causes aspiration of the liquid sample into the needle, process 34 which causes transport of the pipetting needle to the mixing chamber 14, process 35 which causes ejection of the liquid sample from the pipetting needle into the mixing chamber, and process 36 which causes transport of the pipetting needle back to a rest or starting position.

Each of processes 31 to 35 includes a process for monitoring it.

For this purpose, monitoring sensors are associated with the means for carrying out each of the respective processes 31 to 35. These sensors are of the following types: for process 31 there is a pressure sensor; for process 32 there is a sensor for immersion detection; for process 33 there is a pressure sensor; for process 34 there is a sensor for immersion detection (retroactive); and for process 35 there is a pressure sensor or an optical sensor.

The control and monitoring of each of sequences 31 to 35 is effected by associated operation and monitoring control units which operate independent from each other and which use stored data, and in particular, threshold values obtained from previous measurements and tests with characteristic liquids.

Generally, the actual sensor values are compared to the associated threshold values to determine whether the respective actual sensor values are greater, equal, or smaller than the threshold values.

In FIG. 2, each of the blocks 31–36 represents the sequence of operations of the respective processes defined above and also the means, that is the operation and monitoring control unit, for carrying out that process.

A comprehensive and complex flow and decision diagram corresponds to each of the processes 31 to 35, respectively, and to the operation and monitoring control unit used for carrying out such processes. For instance, FIG. 3 shows the diagram of a process included in process 33 for monitoring pressure variations related to sample aspiration.

Figure 3:
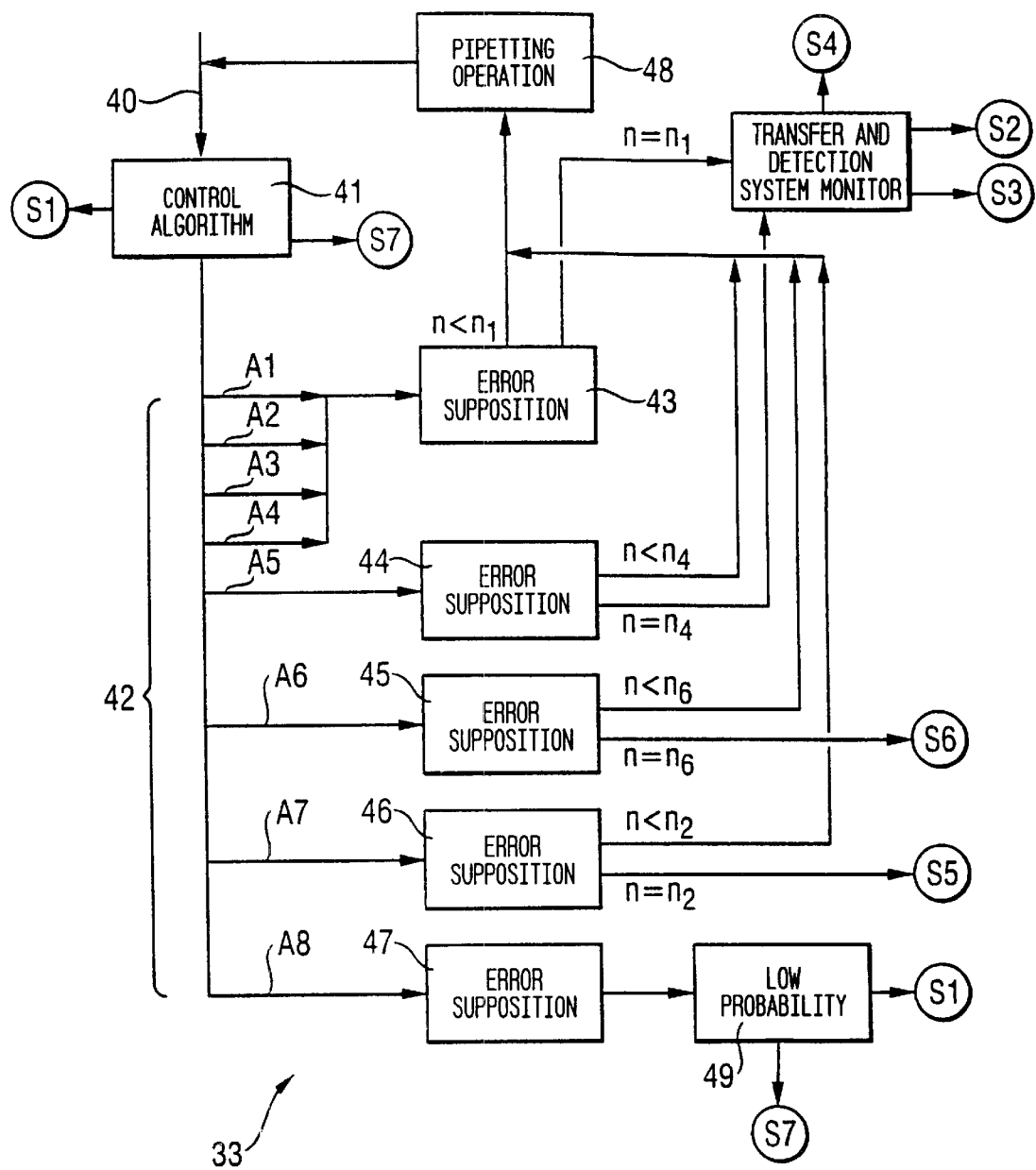
FIG. 3 shows a flow and decision diagram of a process for monitoring pressure variations related to sample aspiration in a pipetting process.

As shown by the diagram in FIG. 3, the process starts upon reception of a start command 40 which starts a process according to control algorithm 41. The pipetting needle is first displaced to the corresponding sample container at a relatively high speed. The tip of the pipetting needle is subsequently immersed into the liquid sample in a controlled manner. The liquid sample is aspirated into the needle and then the needle is retracted from the sample. Meanwhile, the monitoring pressure measurements yield pressure values $P_1$, $P_2$, $P_3$, and $P_4$. These different pressure values result from acceleration forces acting upon the liquids in the metering system and from fluid resistance which is influenced by the liquid content of the pipetting needle.

If the pressure values $P_1$ to $P_4$ are in the range of the associated stored threshold values, the mode signal S1 is delivered which represents the result "no error". Otherwise, one or a plurality of deviations A1 to A8 are involved. These deviations originate from different causes. For example, if the pressure falls below a predetermined threshold value during the movement of the pipetting needle, a partial or complete obstruction of the needle may be the cause. On the other hand, if the pressure is equal to ambient pressure during the entire movement of the needle, this may be the result of a substantial leak or of the absence of a movement due to a motor failure. Other deviations may, for instance, be the absence of a pressure drop after the aspiration of the liquid into the pipetting needle and before the emergence of the latter from the liquid.

Based on experience, it is assumed that for the majority of deviations A1 to A7, the cause of the error can be eliminated by repetition of the respective operation. Therefore, another pipetting operation 48 is requested in the case of error suppositions 43 to 47, which is equivalent to a new start 40. If pressure values $P_1$ to $P_4$ in the desired range are obtained in this operation, the output is mode signal S1.

Otherwise, after $n_1$, $n_2$, $n_4$, and $n_6$ repetitions, respectively, mode signals S2, S3, S4, S5, or S6 are obtained which indicate or S6 are obtained which indicate concrete errors, e.g. $n_1=3$; $n_2=3$; $n_4=3$; $n_6=2$.

Mode signal S2, S3 and S4 represents a possible disturbance of the transfer.

Mode signal S7 indicates that the reliability of a measurement result is reduced.

Mode signal S4 represents a possible disturbance of the transfer.

As illustrated in FIG. 3, error supposition 43 is triggered by error A1, error A2, error A3 or error A4.

Similarly, error supposition 44 is triggered by error A5; error supposition 45 is triggered by error A6; error supposition 46 is triggered by error A7; and error supposition 47 is triggered by error A8.

Deviation A8 is a marginal case where there is a "low probability" 49 of an error. In this case, mode signal S1 is output which results in an uninterrupted operation of automatic analyzer 10.

A total of seven different mode signals S1 to S7 are defined for automatic analyzer 10. Table 1 indicates the status of the analyzer associated with these signals as well as the corresponding reaction of the control of the apparatus. Therefore, mode signals S1 to S7 are in fact interface commands which enable a cooperation of the abovementioned monitoring process which are independent from each other.

TABLE 1

| Mode signal | Status (simplified) | Reaction |
|---|---|---|
| S1 | The sequence of operations is correct. No error is detected. | Terminate the sequence of operations without delivery of an error message. Go to the next sequence. |
| S2 | When the analyzer is initialized, an error is detected by the detection system and operation is not terminated correctly. | Terminate the sequence of operations with delivery of an error message. Go to the next sequence. |
| S3 | When the analyzer is initialized, the detection system is switched off or an error is detected by the detection system. The sequence of operations is not correctly terminated. The detection system remains switched on. | Deliver an error message. Interrupt the sequence. |
| S4 | In run mode of the analyzer, there is an error in the detection system. | Stop after processing pipetted sample. |
| S5 | n times the same error | Single out the concerned sample. Deliver an error message. |
| S6 | n times the same error | Single out the concerned cup. Deliver an error message. |

TABLE 1-continued

| Mode signal | Status (simplified) | Reaction |
|---|---|---|
| S7 | The reliability of a measurement result is reduced. | The output result is flagged. |

Figure 4:
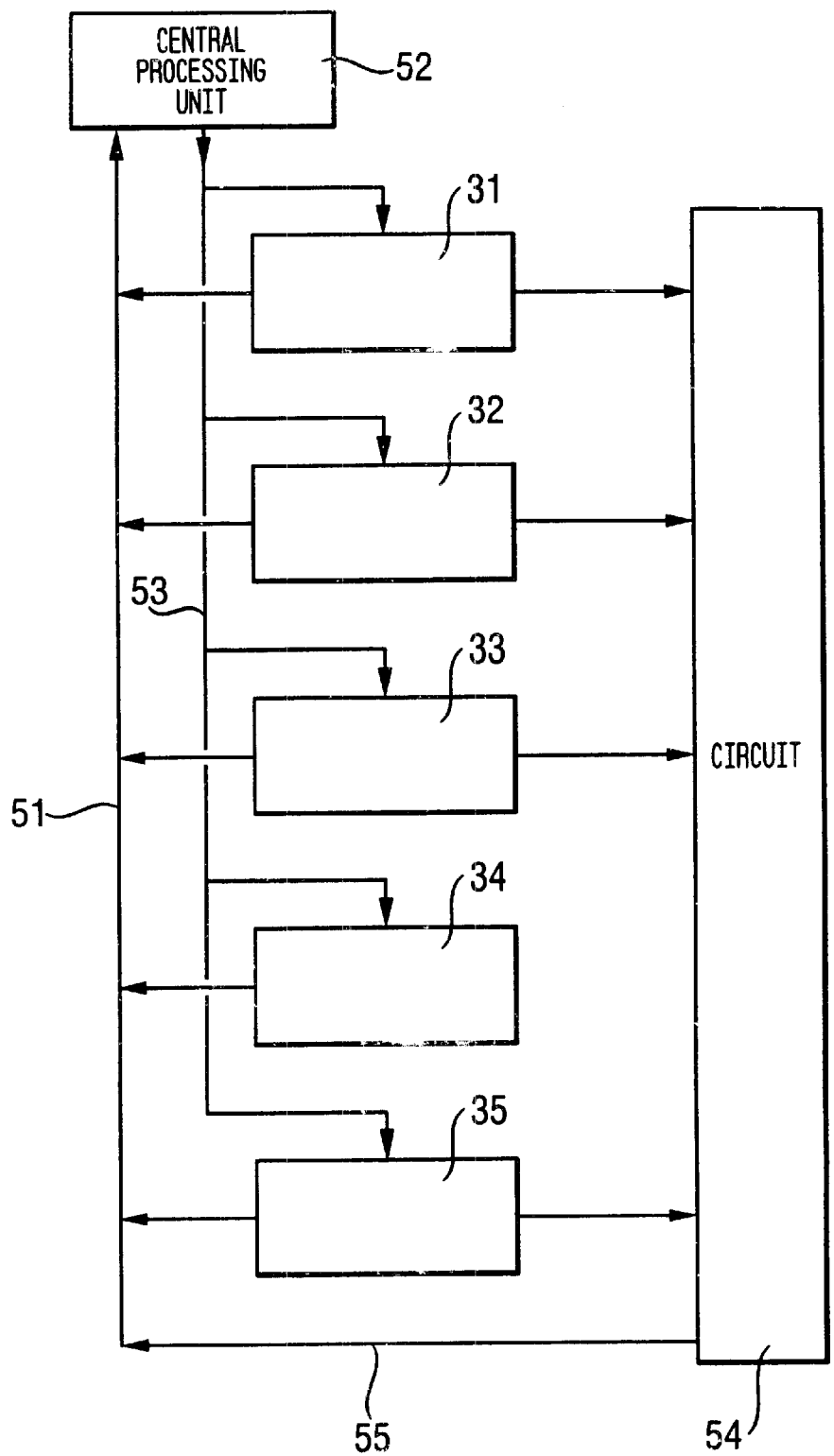
FIG. 4 shows a schematic diagram of the cooperation of independent monitoring processes each related to one of the sequences of operations 31–35 represented in FIG. 2.

FIG. 4 shows a diagram of cooperation between monitoring processes which are independent from each other. As in FIG. 2, each of the blocks 31–36 (block 36 not shown) also represents the sequence of operations of the respective process and the operation and monitoring control unit for carrying out that process.

The cooperation of these monitoring processes constitutes an overall plausibility check. In the case of a statement indicating reduced reliability, e.g. "an air bubble has been ejected during ejection of the liquid sample from the pipetting needle into cuvette 14," this monitoring process serves to obtain a more founded assertion to obtain an unambiguous mode signal S1 to S7.

In accordance with FIGS. 3 and 4, at the end of each of processes 31 to 35 a respective mode signal S1 to S7 is provided to a central processing unit 52 on a line 51. The reply of the central processing unit is a start signal on a second line 53 for the next process 32 to 35 in the succession. In the case of deviations 42 (FIG. 3), sequences 31 to 35 deliver corresponding messages to a combinatory logic circuit 54 (FIG. 4). The circuit 54 combines the messages in the sense of a logical AND, thereby obtaining either a positive (or O.K.) indication or an error message which is output in the form of an output signal to line 51 via output terminals. It is possible, particularly in doubtful cases, to obtain unambiguous commands and statements which allow quick and objective action.

Reactions of the analyzer each of which corresponds to each one of the mode signals (S1 to S7) being provided in the central processing unit 52, e.g. in the form of a list of commands.

The pressure sensors for the monitoring of sequences 31, 33, and 35 indicated in FIG. 2 can be selected and suitably positioned in analyzer 10 (FIG. 1) according to practices known to those skilled in the art. These sensors can recognize the immersion of the tip of the pipetting needle (which is part of the monitoring of process 32) and detect the presence of foam which may be on top of the pipetted liquid sample, thereby essentially reducing the risk of aspirating bubbles into the pipetting needle.

The optical sensor for monitoring process 35 (FIG. 2) may be in the form of a light barrier extending transversally to the ejection direction of the liquid and thus taking advantage of the different refraction properties of the bubbles and liquid.

According to FIG. 4, operating and monitoring control units 31 to 35 are each a self-contained unit. These units are independent from each other. Each one of these units can be activated by a specific start command and in response thereto carries out the sequence of operations and delivers an output signal (one of S to S7) to central processing unit 52. The number of processes 31–35 may be chosen as desired. Hence, this number may be greater or smaller than the number of five shown in FIG. 4. Furthermore, the inner structure of the operation and monitoring control units 31 to 35 may be designed as desired. The structure of such a unit may be in the form of a discrete electronic control circuit. However, the preferred structure of such a unit is in the form of a self-contained program for a program-controlled processor.

Based on practical considerations, a preferred number of mode signals S1 to S7 has been found to be seven. However, this number may be greater or smaller than seven. In this context, it is important to have the clearest possible definition of the associated states and of the reactions of the analyzer in order to respond to all conceivable errors.

Numerous modifications and alternative embodiments of the invention will be apparent to those skilled in the art in view of the foregoing description. Accordingly, this description is to be construed as illustrative only and is for the purpose of teaching those skilled in the art the best mode of carrying out the invention. Details of the apparatus may be varied substantially without departing from the spirit of the invention and the exclusive use of all modifications which come within the scope of the appended claims is reserved.

What is claimed is:

1. An automatic analyzer for the assay of liquid samples, said analyzer comprising:

a pipetting device for removing said liquid sample from a container and for transferring the sample, a mixing chamber having a reaction cuvette for receiving said sample, means for controlling the operation of the analyzer, sensors for monitoring the function of the analyzer, means for evaluating possible monitoring results and for delivering possible error messages, said means including at least one program-controlled processor, a plurality of operation and monitoring control units which are independent from each other, a central processing unit for activating each of said control units by a start command and for carrying out a process which ends with the delivery of a corresponding mode signal (S1 to S7) to said central processing unit, and a combinatory logic circuit which is connected to at least two of said control units, said logic circuit combining messages delivered by said control units as a logical AND and delivering to said central processing unit an output mode signal which corresponds to the combinatory result, and reactions of the analyzer each of which corresponds to each one of the mode signals (S1 to S7) being provided in said central processing unit.

2. The analyzer of claim 1, wherein said analyzer further comprises:

a first unit that causes and monitors rinsing a pipetting needle;

a second unit that causes and monitors a controlled immersion of the pipetting needle into a liquid;

a third unit that causes and monitors aspiration of liquid into the pipetting needle, and a fourth unit that causes and monitors ejection of the aspirated liquid from the pipetting needle.

3. The analyzer of claim 2, wherein said analyzer further comprises an optical sensor to monitor the ejection of the aspirated liquid from the pipetting needle.

4. The analyzer of claim 1, wherein said control units and said combinatory logic circuit are discrete electronic circuits.

5. The analyzer of claim 1, wherein said control units and said logic circuit are self-contained programs associated with a superior control program for a program-controlled processor.

\* \* \* \* \*